United States Patent
Suaning

(10) Patent No.: US 10,086,200 B2
(45) Date of Patent: Oct. 2, 2018

(54) NEURAL STIMULATION ELECTRODES

(75) Inventor: Gregg Jorgen Suaning, Lisarow (AU)

(73) Assignee: NewSouth Innovations Pty Limited, Sydney, New South Wales (AU)

( * ) Notice: Subject to any disclaimer, the term of this patent is extended or adjusted under 35 U.S.C. 154(b) by 0 days.

(21) Appl. No.: 14/342,365

(22) PCT Filed: Aug. 31, 2012

(86) PCT No.: PCT/AU2012/001027
§ 371 (c)(1),
(2), (4) Date: Jul. 23, 2014

(87) PCT Pub. No.: WO2013/029111
PCT Pub. Date: Mar. 7, 2013

(65) Prior Publication Data
US 2014/0330343 A1    Nov. 6, 2014

Related U.S. Application Data

(60) Provisional application No. 61/540,088, filed on Sep. 28, 2011.

(30) Foreign Application Priority Data

Aug. 31, 2011 (AU) ................ 2011903509

(51) Int. Cl.
*A61N 1/36* (2006.01)
*A61N 1/05* (2006.01)
(52) U.S. Cl.
CPC ....... *A61N 1/36046* (2013.01); *A61N 1/0543* (2013.01)
(58) Field of Classification Search
CPC .... A61B 2018/1467; A61B 2018/0016; A61B 2018/124; A61B 2018/1253;
(Continued)

(56) References Cited

U.S. PATENT DOCUMENTS 6,458,157 B1    10/2002  Suaning
6,505,078 B1    1/2003   King
(Continued)

FOREIGN PATENT DOCUMENTS

EP          2 200 703 A1      6/2010
WO      WO 2007/006376 A2    1/2007
WO      WO 2013/029111 A1    3/2013

OTHER PUBLICATIONS

Supplementary European Search Report for corresponding European Patent Application No. 12828915, 1 pg., (dated Mar. 9, 2015).
PCT Notification Concerning Transmittal of International Preliminary Report on Patentability (Chapter I of the Patent Cooperation Treaty) for PCT Counterpart Application No. PCT/AU2012/001027, 7 pgs., (dated Mar. 13, 2014).
(Continued)

*Primary Examiner* — Deborah Malamud
(74) *Attorney, Agent, or Firm* — Womble Bond Dickinson (US) LLP

(57) ABSTRACT

The present invention relates to a neural prosthesis. In its most general form, the neural prosthesis comprises an electrode array including a stimulating electrode (801) and a bipolar return electrode (802). The neural prosthesis also comprises a monopolar return electrode (806), a first electrical return path (812) associated with the bipolar return electrode (802) and a second electrical return path (814) associated with the monopolar return electrode (806) wherein, in use, the stimulating electrode (801) provides a stimulating current to the tissue of a recipient and a total return current is divided between a first current in the first electrical return path (812) and a second current in the second electrical return path (814).

10 Claims, 10 Drawing Sheets

(58) Field of Classification Search
CPC .... A61B 2018/165; A61B 2018/00434; A61B 2018/0072; A61B 18/16; A61B 2018/1246; A61B 5/04001; A61B 2562/0209; A61N 1/05; A61N 1/36185; A61N 1/3605; A61N 1/375; A61N 1/36; A61M 2205/054

See application file for complete search history.

(56) References Cited

U.S. PATENT DOCUMENTS

| | | | |
|---|---|---|---|
| 7,734,352 | B2 | 6/2010 | Greenberg et al. |
| 7,877,148 | B2 | 1/2011 | Chowdhury et al. |
| 2006/0095108 | A1 | 5/2006 | Chowdhury et al. |
| 2007/0255319 | A1 | 11/2007 | Greenberg et al. |
| 2008/0065167 | A1* | 3/2008 | Boggs et al. ............ 607/39 |
| 2008/0125833 | A1* | 5/2008 | Bradley ............ A61N 1/08 607/60 |
| 2009/0287275 | A1 | 11/2009 | Suaning et al. |

OTHER PUBLICATIONS

PCT Notification of Transmittal of the International Search Report and the Written Opinion of the International Searching Authority, or the Declaration for PCT Counterpart Application No. PCT/AU2012/001027, 10 pgs., (dated Oct. 29, 2012).

Socrates Dokos, et al., "A Bidomain Model of Epiretinal Stimulation", IEEE Transactions on Neural Systems and Rehabilitation Engineering, vol. 13, No. 2, pp. 137-146, (Jun. 2005).

Miganoosh Abramian, et al., "Activation of Retinal Ganglion Cells following Epiretinal Electrical Stimulation with Hexagonally Arranged Bipolar Electrodes", Journal of Neural Engineering, vol. 8, 12 pgs., (2011).

G.J. Suaning, et al., "An Efficient Multiplexing Method for Addressing Large Numbers of Electrodes in a Visual Neuroprosthesis", Proceedings of the 26th Annual International Conference of the IEEE EMBS, San Francisco, CA, USA, pp. 4174-4177, (Sep. 1-5, 2004).

* cited by examiner

NEURAL STIMULATION ELECTRODES

CROSS-REFERENCE TO RELATED APPLICATIONS

This patent application is a U.S. National Phase Application under 35 U.S.C. § 371 of International Application No. PCT/AU2012/001027, filed Aug. 31, 2012, entitled NEURAL STIMULATION ELECTRODES, which claims priority to Australian Patent Application No. 2011903509, filed Aug. 31, 2011, and U.S. Provisional Patent Application No. 61/540,088, filed Sep. 28, 2011.

FIELD OF THE INVENTION

The present invention relates to electronic neuroprostheses. In one form the invention relates to neural stimulation electrodes for retinal prostheses.

BACKGROUND OF THE INVENTION

Retinal prosthetic devices may use electrode arrays to deliver electrical pulses to the retina in order to evoke patterned light perception. The electrodes evoke perception of phosphenes via remaining intact retinal neurons of vision-impaired users. One problem with implementing these electrode arrays is the trade-off between high density of electrodes providing better visual acuity in the implant recipient and the interference between adjacent stimulating electrodes. Consequently improved methods of implementing electrode arrays are desirable in order to effect neural stimulation through the elicitation of substantially discrete phosphenes.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect the invention provides a neural prosthesis comprising: an electrode array comprising a stimulating electrode and a bipolar return electrode; and a monopolar return electrode; a first electrical return path associated with the bipolar return electrode; and a second electrical return path associated with the monopolar return electrode; wherein, in use, the stimulating electrode provides a stimulating current to the tissue of a recipient; and a total return current is divided between a first current in the first electrical return path and a second current in the second electrical return path.

The electrode array may comprise a plurality of bipolar return electrodes spatially arranged around the stimulating electrode wherein the first electrical return path is associated with the plurality of bipolar return electrodes.

The second return current may be approximately three times larger than the first return current.

The neural prosthesis may also comprise a controller to set a ratio of the first return current to the second return current.

The electrode array may also comprise a plurality of stimulating electrodes having an associated plurality of bipolar return electrodes.

In another aspect the invention provides a method for neural stimulation comprising: providing a stimulating current via a stimulating electrode in an implanted electrode array; providing a first return path via a bipolar return electrode in said electrode array; and providing a second return path via a monopolar return electrode.

The first return path may be associated with a plurality of bipolar return electrodes spatially arranged around the stimulating electrode.

A ratio of a first return current in the first return path to a second return current in the second return path may be around 1:3.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
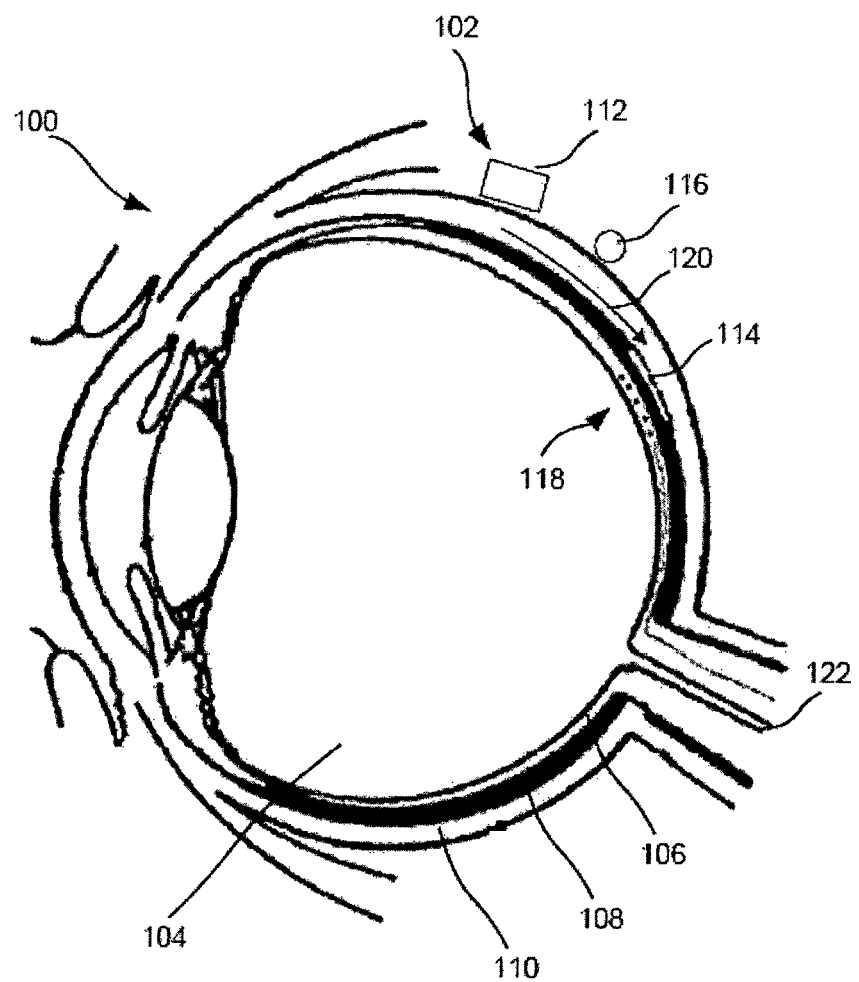
FIG. 1 is a schematic cross-sectional view of an eye with an example of an implanted neural prosthesis.

FIG. 1 shows a cross section of an eye 100 with the implanted portion of a retinal prosthesis 102. The eye 100 includes three layers bounding the vitreous humour 104: the neural retina 106, choroid 108 and sclera 110.

The prosthesis 102 includes at least one electronics capsule 112, an electrode array 114 and a monopolar return electrode 116. When implanting these components of the prosthesis the electrode array 114 is inserted into the eye to be near to the neurons 118 that lie in the neural retina 106 and that need to be stimulated. However, the choroid 108 is the vascular layer of the eye so that incisions may result in unwanted bleeding. Therefore, one method of inserting the electrode array 114 without penetrating the choroid 108 is to make an incision through the sclera 110, for example proximate the electronics capsule 112, and to slide the array along the interface between the sclera 110 and the choroid 108, for example in the direction of arrow 120 until the electrode array is in the desired location, adjacent the necessary neurons 118 but on the opposite side of the choroid 108. In this configuration stimulating pulses from the electrode array 114 may stimulate the neurons 118 from across the choroid. Thus, there is a physical distance between the electrode array 114 and the neurons 118.

When signals are transmitted to the eye for neural stimulation, electrical impulses or stimuli are presented to the eye by injecting electrical current from the electrode array 114 into the tissue, and the current is returned to the implant circuitry via one or more of the electrodes in the array 114, and/or the monopolar return electrode 116. In this way the neurons 118 are stimulated so that they contribute to the perception of phosphenes. Information within the neurons 118 passes to the user's brain via the optic nerve 122.

Figure 2:
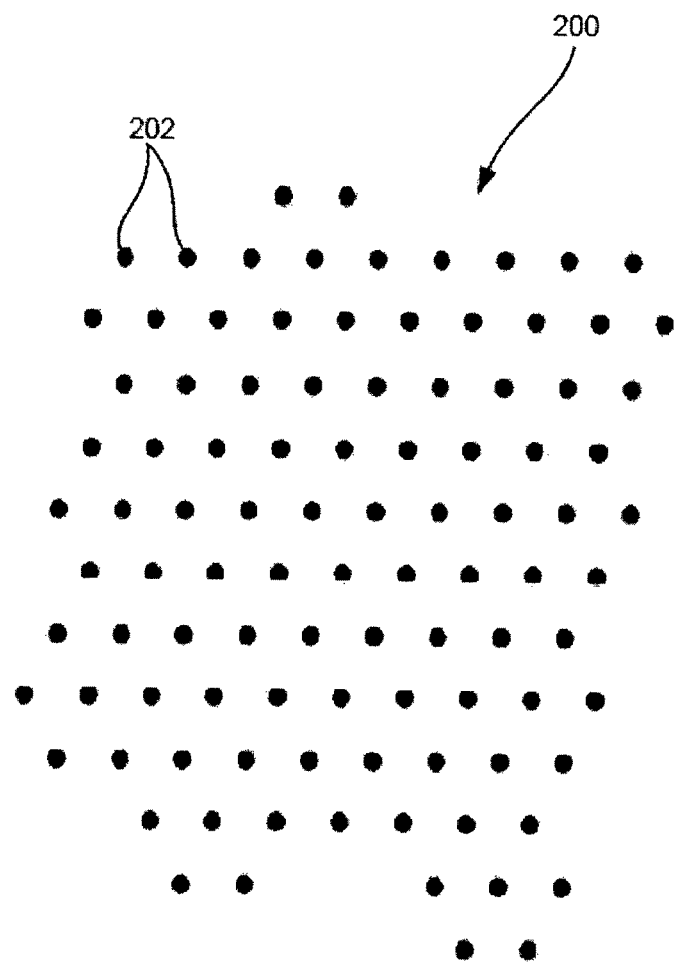
FIG. 2 is a plan view of an example of an electrode array.

A high density of electrodes may provide a high density of phosphenes thereby allowing better visual acuity in the implant recipient. However, if any two regions of activation are too close, injected charge may interfere. Arranging individual electrodes 202 in a staggered geometric array 200 as shown in FIG. 2 allows for high density of phosphenes. When providing stimuli, the electrodes need to be addressed in some way to be able to provide the required stimulus.

Figure 3:
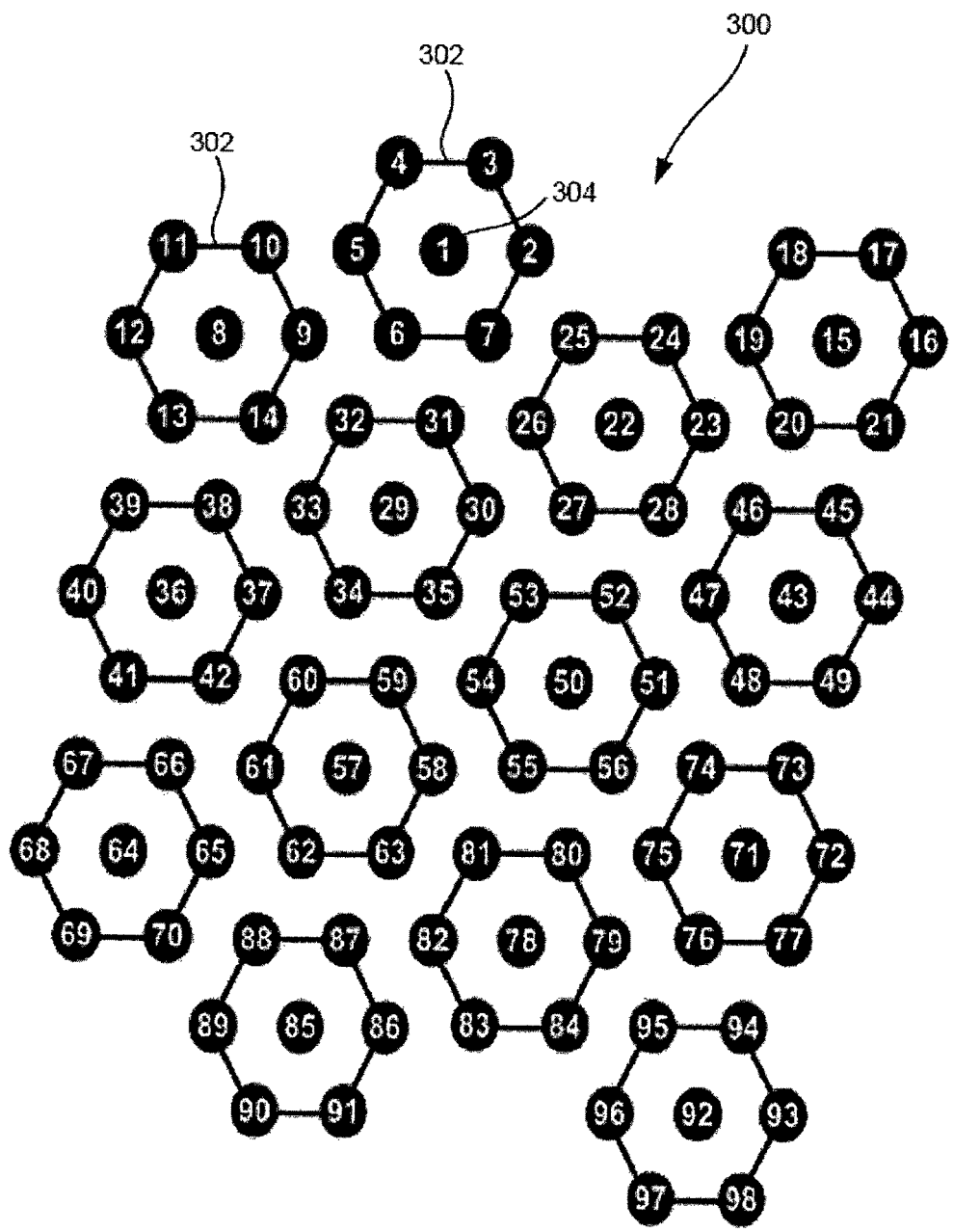
FIG. 3 is a schematic representation of the electrode array of FIG. 2 with a superimposed hexagonal logical array used for addressing.

One method of addressing the electrodes, as described in US patent application number US2009/0287275, the contents of which are incorporated herein by reference, comprises using a superimposed logical array 300 as shown in FIG. 3. This scheme has the advantage of enabling individual electrodes to be addressed in parallel to facilitate parallel stimulation. Repeating regular patterns, here hexagonal shapes 302, are overlaid on the physical electrode array 200. Each of the hexagons 302 contains seven electrodes 202. A numbering scheme, for example that shown in FIG. 3, is used to specify the centre of each hexagon so that the centre of each hexagon is separated from the centres of the adjacent hexagons throughout the array. In the addressing scheme, a single stimulation identifier is used to specify the stimulating electrodes within a plurality of the hexagons. This provides an efficient system for addressing the electrode array.

The centre of each hexagon 302, for example electrode 304, serves as the stimulating electrode, and is associated with a power source that may be located in the electronics capsule 112. One, two or all of the immediately adjacent electrodes (the electrodes at the corners of the hexagons 302) and/or a distant monopolar return path electrode 116 serve as the electrical return path for the current stimulus. During the first phase of biphasic stimulus, the centre electrode 304 in the hexagon 302 is connected to the power sources associated with its respective hexagon. Return path electrodes are connected to either a supply voltage or to a current or voltage sink. During the second charge recovery phase of biphasic stimulation, the electrical connections of the centre electrode and the return path are reversed.

Figure 4:
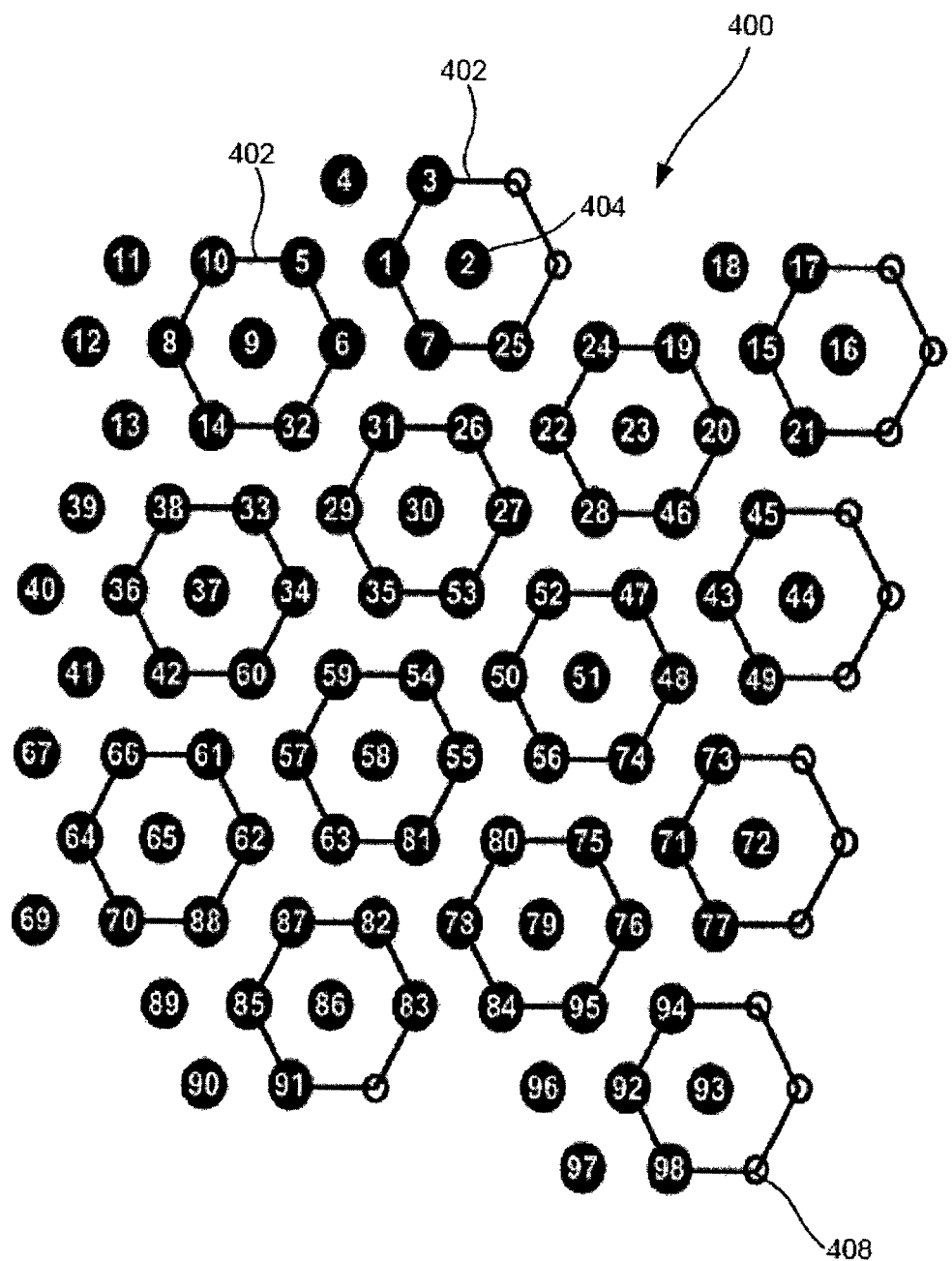
FIG. 4 is the electrode array of FIG. 2 with the superimposed hexagonal array of FIG. 3 shifted by one position.

For different stimulating paradigms, different electrodes in the array 200 are selected to be the stimulating electrodes. This is done by superimposing different logical arrays on the electrode array 200. For example, repositioning the logical array to obtain hexagon array 400 shown in FIG. 4 ensures that different electrodes are placed at the centre of each hexagon 402, such as electrode 404. In logical array 400 the hexagons at the edge of the physical array 200 are incomplete and include unpopulated positions 408. By repositioning the logical array, there exist seven different ways to orient a hexagonal logical array on the electrode array 200, of which two ways are shown in FIGS. 3 and 4.

Figure 5:
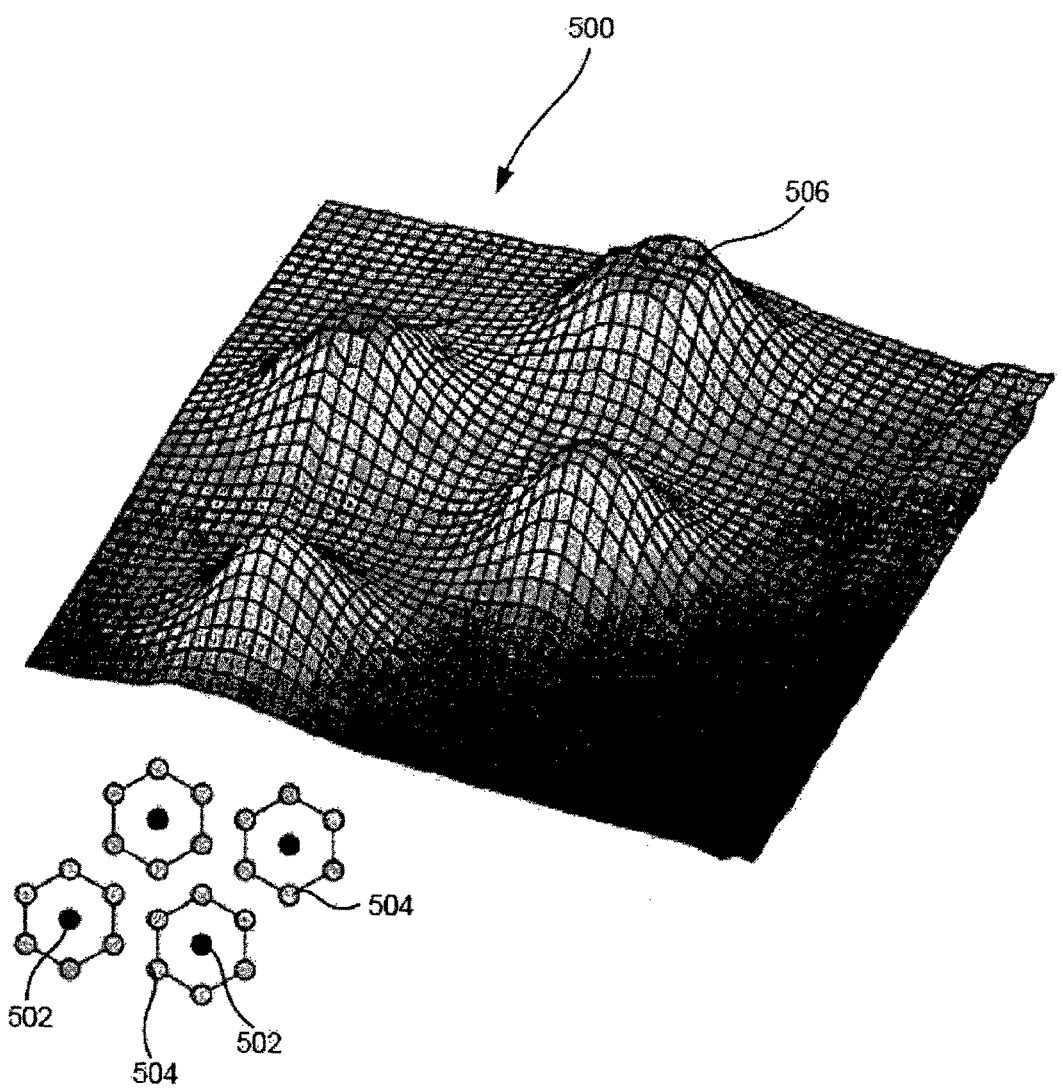
FIG. 5 shows a measured voltage topography resulting from the use of four stimulating electrodes with guard rings.

One consequence of arranging the electrodes in hexagonal groups is that each active electrode is surrounded by up to six electrodes that can function as return electrodes. When all or most of the six are used to collectively return the current delivered to the stimulating electrode then the electrodes surrounding the active electrode can be considered to be "guard electrodes", or a "guard ring" because they limit the spatial distribution of the electrical field generated by the active electrode. FIG. 5 shows a measured voltage topography 500 resulting from the use of four stimulating electrodes 502 with guard electrodes 504. The discrete peaks 506 in the electrical field illustrate how the guard rings result in a limited area being stimulated by each electrode 502 so that little interference occurs between the stimulus from adjacent electrodes 502.

Figure 6:
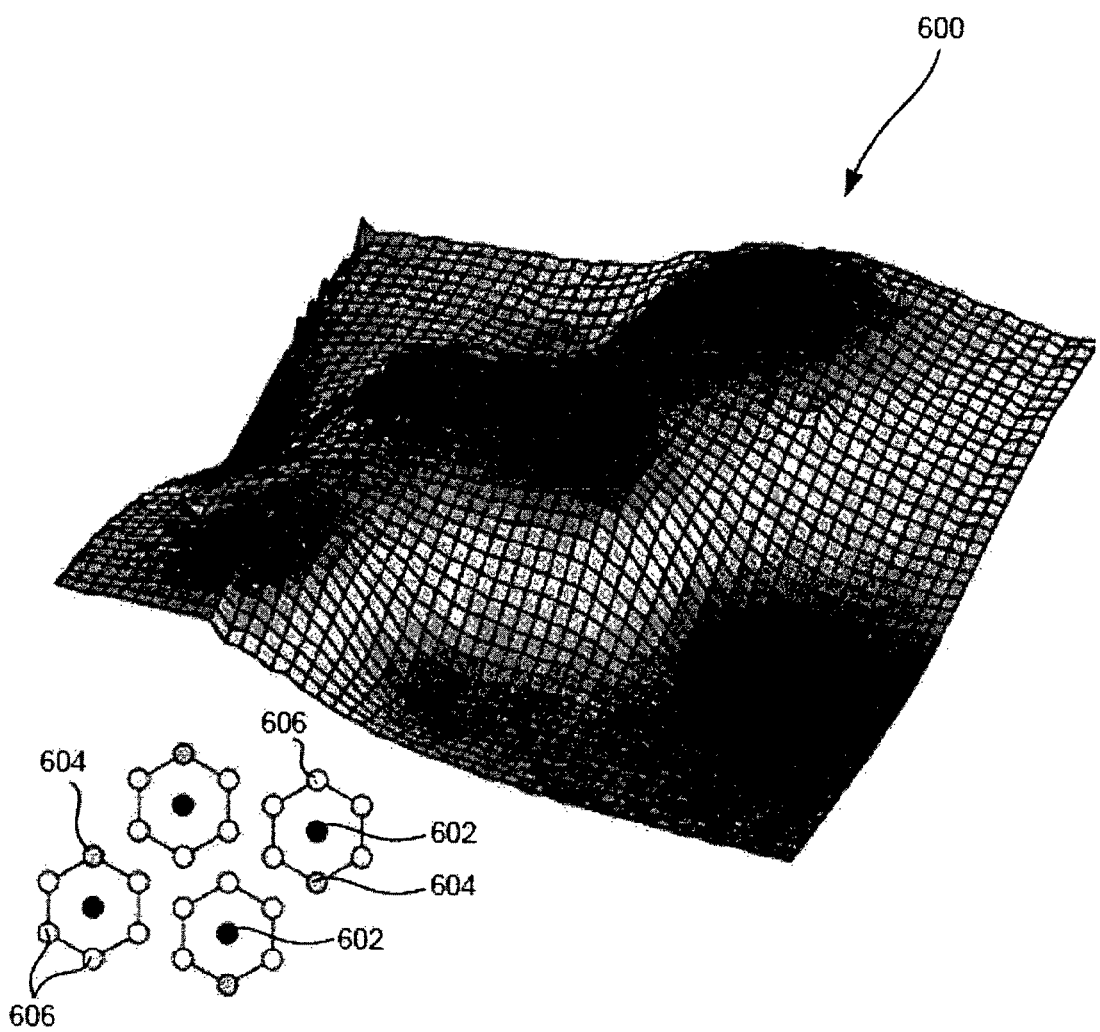
FIG. 6 shows a measured voltage topography resulting from the use of the same four stimulating electrodes as in FIG. 5 with single return paths through one each of the six electrodes surrounding each stimulating electrode.

In contrast, FIG. 6 illustrates a measured voltage topography 600 of four stimulating electrodes 602 with a single hexagon electrode return electrode 604 in each of the four hexagons, while the remaining electrodes 606 are inactive. The interference between the electrical fields resulting from the four stimulating pulses can be seen in the topography 600, in which the peaks are not as distinct as the peaks 506 in FIG. 5.

In the arrangements illustrated in FIG. 5 and FIG. 6, the return paths are provided by electrodes that form part of the hexagons. These electrodes are called "bipolar electrodes" and they can be stimulating electrodes, or form part of the return path. They form "two poles" as opposed to the monopolar situation where there is a single pole involved in the electrical stimulation. The electrodes in the hexagonal patterns can also remain inactive if they are not used in the return path.

In a further arrangement, the central electrodes of the hexagons are used as stimulating electrodes, and a separate monopolar electrode that does not form part of the electrode array 200 provides the return path. This is illustrated as monopolar electrode 116 in FIG. 1. Other locations of monopolar electrode 116 may be contemplated. FIG. 1 is merely an illustrative example of a location within the recipient's orbit.

In this arrangement, because all stimulating electrodes share the same return path there will generally be some interference between the electrical fields resulting from the stimulus of each stimulating electrode. Although this interference is not desirable, monopolar electrical stimulation does typically yield lower stimulation thresholds than other return path configurations. The stimulation threshold is the level of stimulation required in order elicit action potentials from the neurons 118.

A monopolar return path is considered to be a return path provided by a monopolar electrode that is spaced at least multiple electrode diameters away from the stimulating electrode/s. In contrast, a bipolar return path is considered to be a return path provided by one or more electrodes that lie within the area of activation of the stimulating electrode array.

Figure 7A:
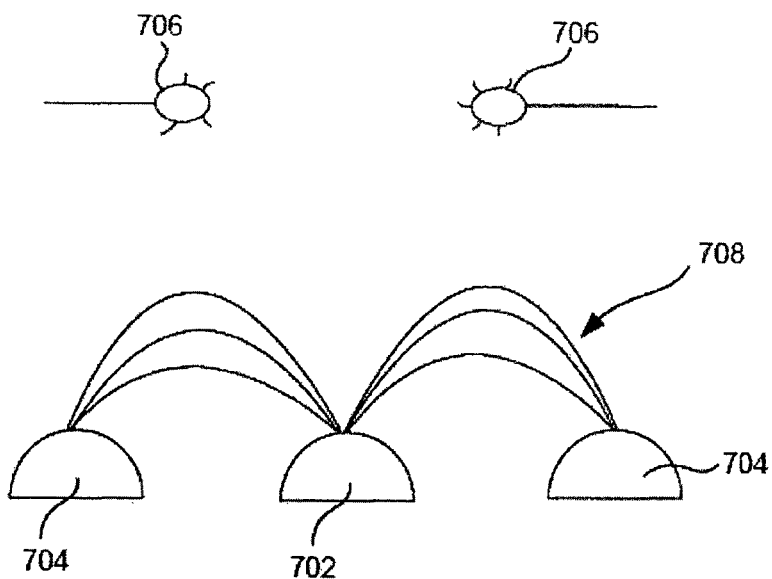
FIG. 7A is a schematic representation of the electrical field resulting from the use of a guard ring configuration.

Referring to FIG. 7A, stimulating electrode 702 and return path electrodes 704 are positioned to lie along the interface between the choroid and the sclera, as described above with reference to FIG. 1. The neurons 706 that need to be stimulated lie in the neural retina of the eye. The hexagonal configuration using the guard ring return path as described above with reference to FIG. 5 results in a reduced electrical field 708 for a given stimulation strength. The stimulation threshold that will result in the electrical field 708 being strong enough to reach the neurons 706 in order to stimulate them is typically higher than for a configuration where the return path is provided through a monopolar electrode.

Figure 7B:
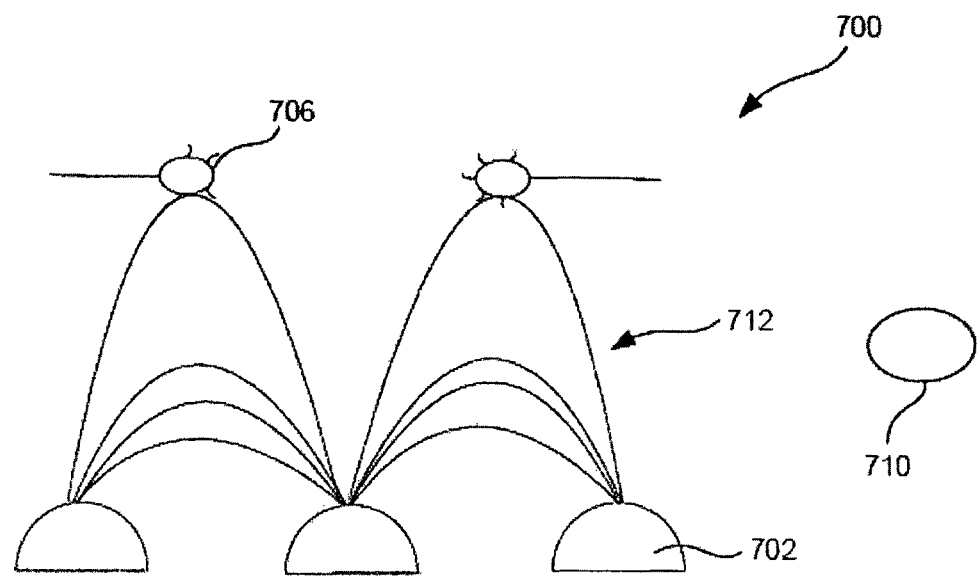
FIG. 7B is a schematic representation of the reshaped electrical field resulting from the use of a hybrid configuration.

However, if a monopolar electrode 710 is added to the hexagonal configuration of FIG. 7A to form a hybrid configuration 700 as shown in FIG. 7B, then the addition of monopolar electrode 710 is thought to result in a local reshaping of the electrical field to provide a reshaped field 712 that is strong enough to reach the neurons 706 even though a similar stimulation strength is being used. In other words, the stimulation threshold of the hybrid configuration is less than the stimulation threshold of the hexagonal guard ring configuration.

Figure 7C:
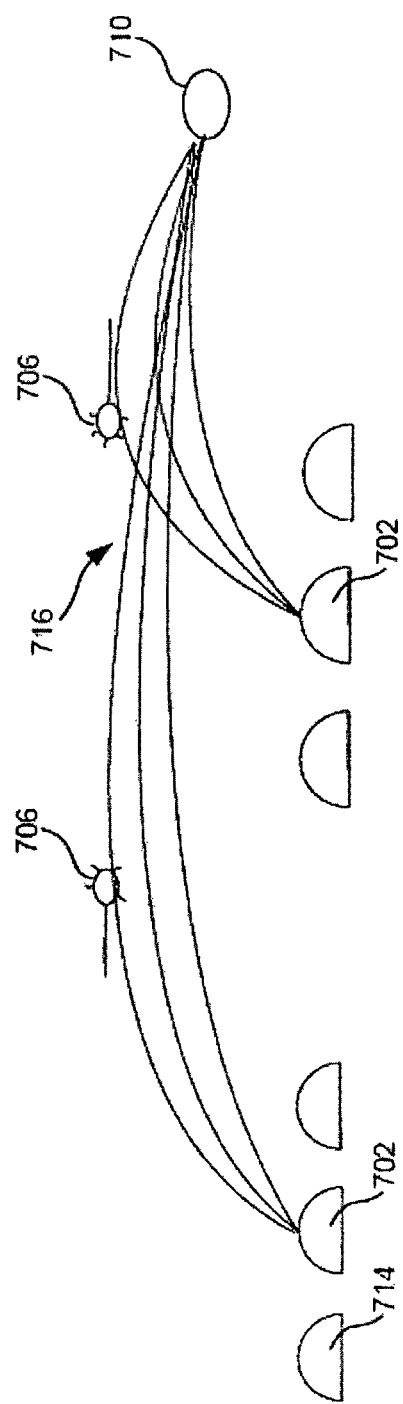
FIG. 7C is a schematic representation of the electrical field resulting from the use of a single monopolar return path.

In FIG. 7C the monopolar electrode 710 provides the only return path when stimulation is applied via electrodes 702 and the "guard" electrodes 714 in the hexagons are inactive. This configuration results in an electrical field 716 with a low stimulation threshold but which suffers from crosstalk. For example, the right-hand neuron 706 may be affected by electrical fields associated with both of the stimulating electrodes 702.

Figure 8:
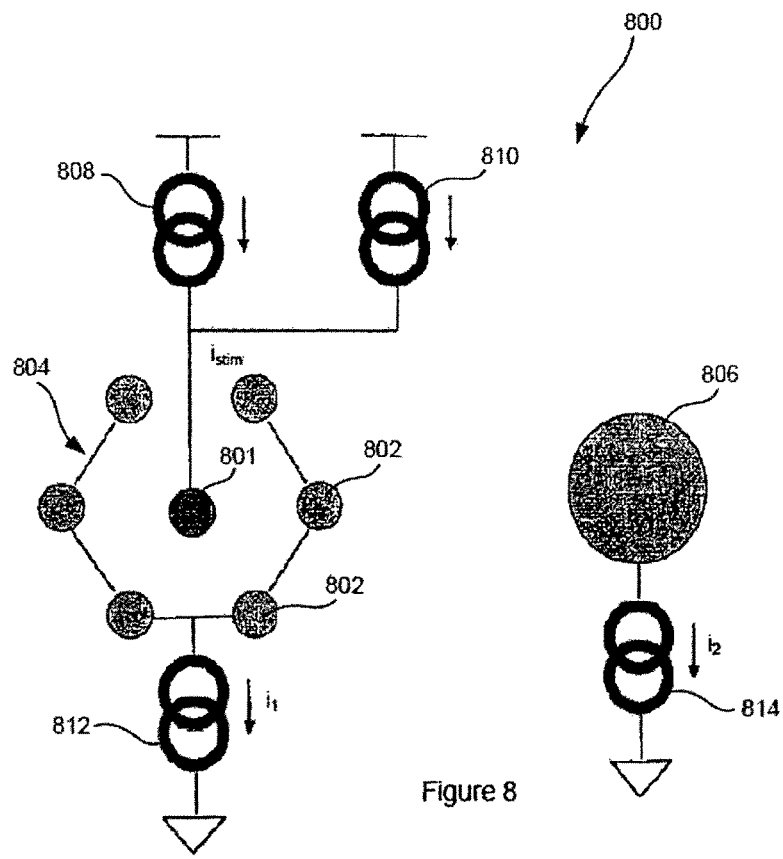
FIG. 8 shows a schematic diagram of an arrangement using a hybrid return path.

In the embodiment of a stimulation circuit 800 shown in FIG. 8, the stimulating current provided by stimulating electrode 801 is provided by current sources 808 and 810. In configuration 800 the return path of the stimulating current provided by stimulating electrode 801 is divided. One or more of the guard electrodes 802 provide part of the return path through current sink 812, and the remainder of the current returns through monopolar electrode 806 and current sink 814. This reduces the required stimulation threshold that is needed to stimulate the neurons because of the use of the monopolar electrode 806. However, the configuration 800 also provides the benefits of charge concentration from the guard electrodes 802 in the hexagon 804.

In this embodiment, the return current through the guard electrodes 802 is $i_1$ and is divided approximately equally through each of these electrodes. The return current through the monopolar electrode 806 is $i_2$. When $i_1=0$, all current that is injected from the stimulating electrode 801 returns via the monopolar electrode 806. In this situation one would anticipate the lowest stimulation threshold to be observed. When $i_2=0$, all current returns via one or more of the hexagon's bipolar electrodes 802. When all six of these electrodes 802 act as return electrodes, as discussed with reference to FIG. 5 for example, then stimulation can occur from multiple sites having respective guard rings simultaneously without significant cross-talk between these sites.

In this embodiment, the stimulating current is divided such that the benefits of threshold reduction are realised by way of the monopolar return path, and the benefits of charge containment through the use of the guard ring electrodes 802 are realised at the same time. The stimulation current is therefore given by $i_{stim}=i_1+i_2$.

Different ratios of $i_1:i_2$ will result in different trade-offs between low stimulation threshold and charge containment, and this depends (amongst other factors) on the diameter of the electrodes that are used. Other factors that influence the ratio used include how far apart the electrodes are from one another because the further apart they are, the less the benefit that may be obtained by the use of the guard ring. Another factor is the thickness of the choroid, which influences the field required.

For example, $i_1$ may be between 10 and 50% of the total return current while $i_2$ is between 50 and 90%. In one embodiment, the return current through the monopolar electrode 806 $i_2$ is approximately 75% of the total return current while the return current through the guard electrodes 802 $i_1$ is approximately 25% of the return current.

In another embodiment there may be additional return paths, for example provided by an additional monopolar electrode. FIG. 8 shows a single hexagon 804. It will be appreciated that the electrode array may include multiple hexagons.

Figure 9:
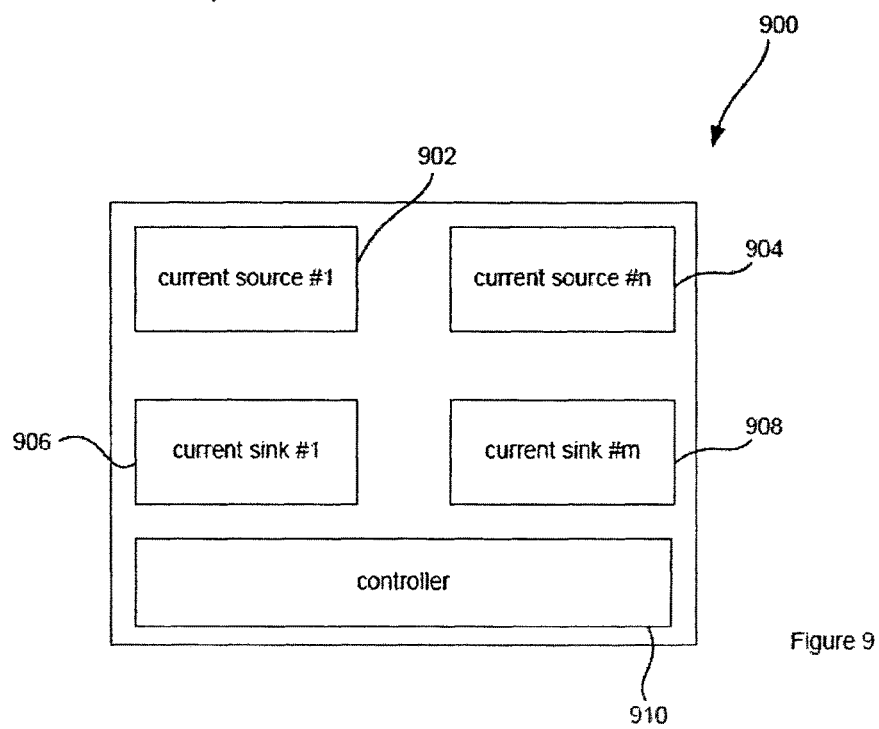
FIG. 9 shows a schematic diagram of the circuitry used to implement the hybrid return path of FIG. 8.

FIG. 9 shows a schematic diagram of the circuitry 900 used to implement the hybrid return path. This circuitry would typically be implemented in the electronics capsule 112 shown in FIG. 1. The circuitry 900 includes at least one current source 902, 904 for association with the stimulating electrodes of the electrode array. For example current source number 1 902 for the first stimulating electrode and current source number n 904 for the $n^{th}$ stimulating electrode. The circuitry 900 further includes at least one current sink 906, 908 for association with the return electrode or return path. For example current sink number 1 may be associated with the guard electrons of a first hexagon while current sink number 2 may be associated with a monopolar return electrode. The circuitry further includes a controller 910 that controls the ratio of the current returned via the respective current return paths used in a hybrid configuration. The controller may be adjustable so as to vary the ratio of the return currents.

Experiments were conducted to study the effects of different ratios of $i_1:i_2$ on the stimulation threshold. In these experiments, a 24-electrode array comprising stimulating platinum electrodes, each of 380 μm in diameter, was used. Of the 24 electrodes, 10 electrodes formed complete hexagons, such as hexagons 302 as illustrated in FIG. 3, whereas the rest of the electrodes were at edges of the array, such as those occupying unpopulated positions 408 as illustrated in FIG. 4. The array was implanted into the suprachoroidal space of the feline eye (with the experiments conducted with n=6 eyes from a total of 5 animals). Following a craniotomy and durotomy, a 10*10 penetrating array (Utah Array, Blackrock Microsystems, Utah, USA) was inserted and connected to a RZ2 multi-channel data acquisition system (Tucker-Davis Technologies, Fla., USA). The retina was stimulated using charge-balanced, constant current, biphasic stimuli with a constant phase time of 500 μs and the resulting cortical activity was recorded. A return current $i_1$ of 700 μA through the guard electrodes 802 (termed hexpolar stimulus) was superimposed with a return current $i_2$ of 0 μA, 37 μA, 72 μA and 108 μA through the monopolar electrode 806 (termed monopolar stimulus). The recordings were filtered and spike counting was performed offline using Matlab (The Mathworks, Inc., USA), and sigmoid curves were fitted to model the effect of increasing stimulation current on the cortical activity. The midpoint on the slope (P50) of the sigmoid was chosen as an arbitrary indication of threshold and the results compared.

Figure 10:
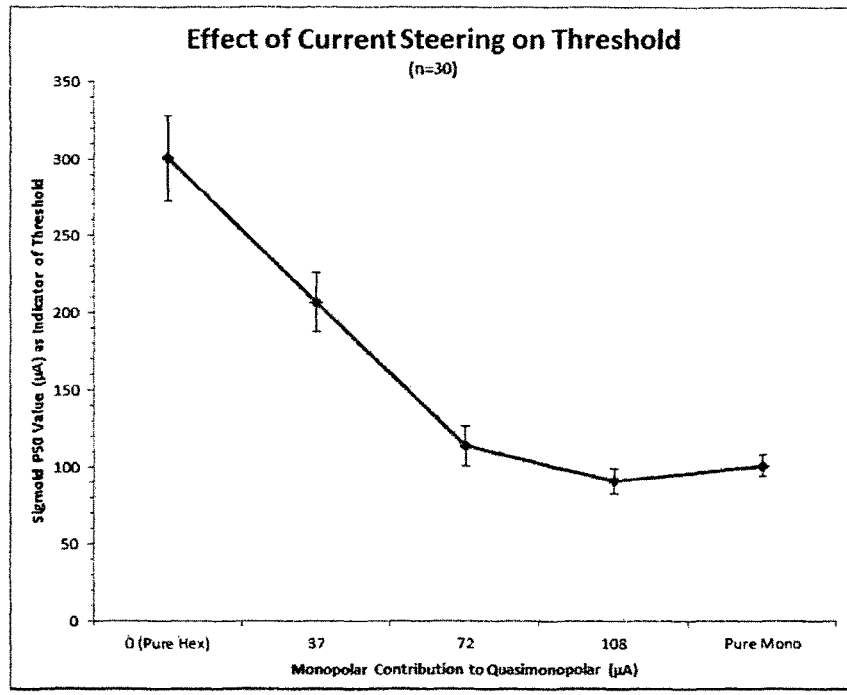
FIG. 10 illustrates experimental results showing the effects on stimulation threshold of different ratios of monopolar and hexpolar stimulation with the bars indicating the standard error.

Referring to the experimental results illustrated in FIG. 10, the first data point where the the monopolar current $i_2$ is 0 µA represents a pure hexpolar stimulus, where all stimulation current returns through the guard electrodes 802 and none returns through the monopolar electrode 806. The stimulation threshold for a pure hexpolar stimulus was determined to be 300 µA±28 µA (standard errors are indicated by the bars in FIG. 10). With the addition of 37 µA of monopolar stimulus represented by the second data point, the stimulation threshold was found to drop by almost a third, to 206 µA±19 µA. At the third data point, 72 µA of monopolar stimulus resulted in a further drop to 113 µA±13 µA. At the fourth data point, 108 µA of monopolar stimulus resulted in a threshold of 90 µA±8 µA. The fifth data point represents a pure monopolar stimulus (i.e. is 0), which resulted in a stimulation threshold of 101 µA±7 µA. In these results the mean stimulation threshold of the fifth data point (that is, for a pure monopolar stimulus) is slightly higher than that of the fourth data point. This is thought to be a data processing artefact and in general it is anticipated that the threshold will be lowest for pure monopolar stimulation. These results indicate that combining monopolar and hexpolar stimuli yields lower stimulation thresholds than using a hexpolar stimulus alone. This is consistent with the presence of monopolar and hexpolar fields around the electrodes, and confirms a superposition effect wherein higher charge density elicits action potentials for a significantly lower overall charge.

Experiments were also conducted to study the effects of different ratios of $i_1:i_2$ on charge containment. A best cortical electrode (BCE) was chosen as the electrode with the highest maximum spike rate and the lowest P50 value. Using the spike counting data collected above, the probability of a spike occurring was calculated on the best cortical electrode (BCE), and then the probability of a spike occurring simultaneously in every other site was calculated using:

$$P(El_x|BCE) = \frac{P(El_x \cap BCE)}{P(BCE)}$$

where $P(El_x|BCE)$ is the probability of a spike occurring at a given site $El_x$ given that it also occurred at the BCE, $P(El_x \cap BCE)$ is the probability of a spike occurring at a site $El_x$ and BCE simultaneously, and $P(BCE)$ is the probability of a spike occurring on the BCE.

In these experiments, using these values, the specific case where $P(BCE)$ attains a maximum value was observed to maximise the spread of the electrical field, and the probability of spikes occurring across all electrodes was observed. If $P(El_x|BCE)$ was greater than 0.5, then the site was considered "active" and that site was counted, otherwise it was ignored. The channels of all stimulation strategies were then normalised with respect to the channel count of a pure monopolar stimulus to eliminate bias introduced by the placement of the stimulating electrode.

Figure 11:
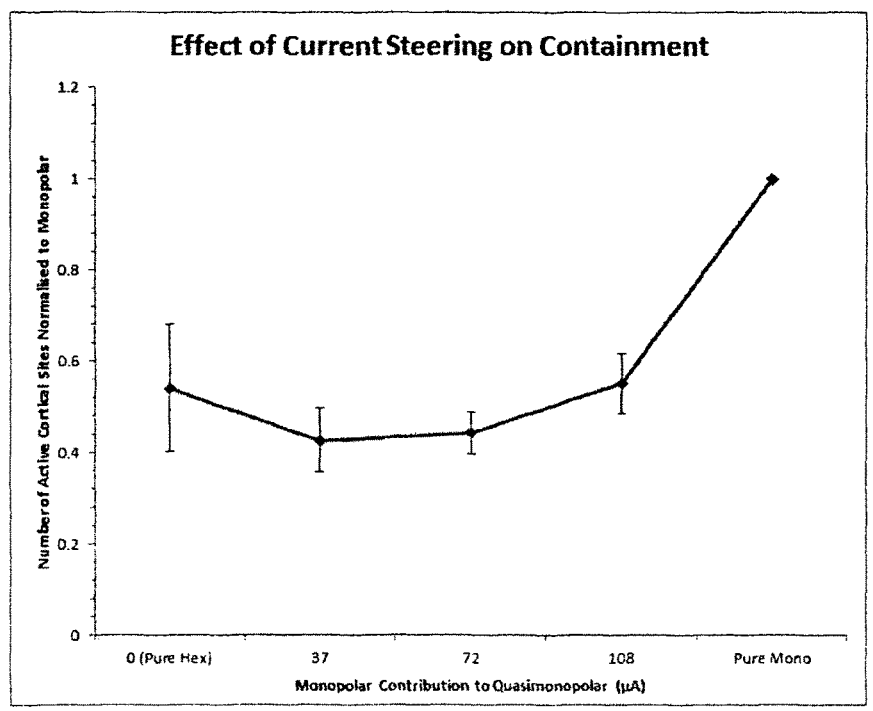
FIG. 11 illustrates experimental results showing the effects on charge containment of different ratios of monopolar and hexpolar stimulation with the bars indicating the standard error.

Experimental results are illustrated in FIG. 11, which are normalised to the case of a pure monopolar stimulus. The guard electrodes in the pure hexpolar arrangement ($i_2$=0 µA) recruited (54±13) % of the number of sites. With the addition of $i_2$=37 µA of monopolar stimulus, the recruitment was (42±7) % of the number of sites. With $i_2$=72 µA and 108 µA of monopolar stimulus, the recruitment was (44±4) % and (55±6) % respectively. FIG. 11 shows that quasi-monopolar stimulus offers significant activation containment with respect to pure monopolar stimulation, and approximates that of hexpolar stimulation.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A neural prosthesis configured for providing stimulating current to the tissue of a recipient, the neural prosthesis comprising:
    an electrode array comprising a stimulating electrode and at least one bipolar return electrode spatially arranged around the stimulating electrode to limit the spatial distribution of the electrical field generated by the stimulating electrode;
    a monopolar return electrode;
    at least one current source to provide a stimulating current to the stimulating electrode to provide a first amperage that corresponds to a stimulation threshold for a hybrid stimulation by the neural prosthesis that is greater than a second amperage that corresponds to a stimulation threshold required for a monopolar stimulation by the neural prosthesis and is less than a third amperage that corresponds to a stimulation threshold required for a bipolar stimulation by the neural prosthesis to generate an electric field that is sufficient to stimulate neurons and decrease interference;
    a first electrical return path for the stimulating current, the first electrical return path comprising the at least one bipolar return electrode and having a first current sink associated with the at least one bipolar return electrode;
    a second electrical return path for the stimulating current, the second electrical return path comprising the monopolar return electrode and having a second current sink associated with the monopolar return electrode; and
    a controller to control the first electrical return path and the second electrical return path whilst the stimulating current is being provided to the stimulating electrode, so as to divide a return current of the stimulating current between the first electrical return path and the second electrical return path such that a first non-zero return current flows into the first current sink and simultaneously a second non-zero return current flows through the second current sink;
    wherein the at least one current source is a controlled current source, configured to provide the stimulating current responsive to received signals for neural stimulation.

2. The neural prosthesis of claim 1 wherein the controller is configured to divide the return current so that the second non-zero return current is approximately three times larger than the first non-zero return current.

3. The neural prosthesis of claim 1 wherein the controller is configured to control the first and second non-zero return currents flowing to the first and second current sinks between any one of a plurality of currents.

4. The neural prosthesis of claim 1 wherein the stimulating electrode is one of a plurality of stimulating electrodes associated with a plurality of respective bipolar return electrodes.

5. A neural prosthesis of claim 1, wherein the controller is configured to control the first non-zero return current to between 10% and 50% of the total return current for the stimulating electrode.

6. The neural prosthesis of claim 1, comprising a plurality of said bipolar return electrodes, wherein the plurality of bipolar electrodes:
   simultaneously each form part of a return path for current from the stimulating electrode; and
   are arranged in an electrode group with the stimulating electrode, the electrode group comprising the plurality of bipolar return electrodes positioned around the stimulating electrode.

7. The neural prosthesis of claim 6, wherein the electrode array comprises a plurality of said electrode groups positioned adjacent to each other.

8. The neural prosthesis of claim 7, wherein the plurality of electrode groups each comprise said stimulating electrode surrounded by six said bipolar return electrodes arranged substantially in a hexagon around the stimulating electrode.

9. The neural prosthesis of claim 1, comprising electronics configured to stimulate the electrode array using biphasic stimulation, the electronics controlling the at least one current source to provide current to the stimulating electrode in one phase of the biphasic stimulation and not the other phase.

10. The neural prosthesis of claim 1, wherein a total return current through the first electrical return path is divided approximately equally between each of a plurality of said bipolar return electrodes.

* * * * *